(12) United States Patent
Sak et al.

(10) Patent No.: US 10,098,617 B2
(45) Date of Patent: Oct. 16, 2018

(54) MEDICAL APPARATUS FOR SAMPLING CERVICAL TISSUE

(71) Applicant: Solocell Corp., Fort Pierce, FL (US)

(72) Inventors: Robert F. Sak, Fort Pierce, FL (US); Richard Alexis Conlen, Highland Beach, FL (US)

(73) Assignee: Solocell Corporation, Fort Pierce, FL (US)

( * ) Notice: Subject to any disclaimer, the term of this patent is extended or adjusted under 35 U.S.C. 154(b) by 331 days.

(21) Appl. No.: 14/821,911

(22) Filed: Aug. 10, 2015

(65) Prior Publication Data

US 2017/0042518 A1 Feb. 16, 2017

(51) Int. Cl.
*A61B 10/02* (2006.01)

(52) U.S. Cl.
CPC .. *A61B 10/0291* (2013.01); *A61B 2010/0216* (2013.01)

(58) Field of Classification Search
CPC .. A61B 10/0291; A61B 10/02; A61B 10/0045
See application file for complete search history.

(56) References Cited

U.S. PATENT DOCUMENTS

| | | | |
|---|---|---|---|
| 5,445,164 A | 8/1995 | Worthen et al. | |
| 5,456,265 A | 10/1995 | Yim | |
| 5,795,309 A | 8/1998 | Leet et al. | |
| 7,087,028 B2 * | 8/2006 | Sak | A61B 10/0045 600/569 |
| 2002/0120214 A1 * | 8/2002 | Cole | A61B 10/0291 600/570 |
| 2013/0066233 A1 * | 3/2013 | Klein | A61B 10/0291 600/572 |
| 2014/0073988 A1 | 3/2014 | McSherry | |
| 2014/0180165 A9 * | 6/2014 | Zwart | A61B 10/02 600/569 |

FOREIGN PATENT DOCUMENTS

WO 2009/018607 A1 2/2009

OTHER PUBLICATIONS

Oct. 26, 2016—(WO) International Search Report—App PCT/US16/46177.
Oct. 26, 2016—(WO) Written Opinion of the International Searching Authority—App PCT/US16/46177.

* cited by examiner

*Primary Examiner* — Sean Dougherty
*Assistant Examiner* — Patrick Fernandes
(74) *Attorney, Agent, or Firm* — Banner & Witcoff, Ltd.

(57) ABSTRACT

A cervical sampling system for collecting a cervical sample for a Pap test. The cervical sampling system includes an insertion tube and an introduction guide member that guides the insertion tube into a vaginal cavity.

19 Claims, 6 Drawing Sheets

MEDICAL APPARATUS FOR SAMPLING CERVICAL TISSUE

FIELD OF INVENTION

The aspects of the disclosure relates to an apparatus and system for obtaining a sample of vaginal tissue such that developing cancerous cells may be detected.

BACKGROUND

Unlike many cancers that cause pain, noticeable lumps, or other early symptoms, cervical cancer has no telltale warning signs until it is so advanced that it is usually unresponsive to treatment. Only in the late stages does cervical cancer cause pain in the lower abdominal or back region, or produce other noticeable symptoms. Tests which provide early detection of cervical, uterine and vaginal cancer are paramount to the effective treatment and recovery from the disease. A Papanicolaou smear test, commonly referred to as a Pap test, has long been established as a highly useful diagnostic tool which allows the identification of premalignant and malignant tissue at very early stages of the disease, as well as the identification of various inflammations and infections. The American Society of Clinical Pathologists recommends women have an annual Pap test.

A Pap test is a clinical procedure in which typically a bivalve speculum is inserted into a vaginal cavity and the cervix is exposed for sampling. A sample smear of cervical or vaginal secretions is then removed using an inserted scraper, probe, brush or similar type of device. The collected smear is evenly spread on one or more glass slides for microscopic examination. These standard-sized laboratory slides may be lined with hundreds of thousands of cervical cells. These slides are examined for the early detection of cancer or to determine the presence of certain hormonal conditions or certain infections. Lurking in these cells may be as few as a dozen abnormal cells. Finding such telltale cells is akin to finding a needle in a haystack, especially at the end of the day when laboratory technicians are likely to have examined countless Pap test slides. In addition, abnormalities in cell shape may be slight and difficult for even the trained eye to detect, or may be masked by infection.

At one time Pap tests were performed almost exclusively by medical professionals in a doctor's office or a hospital. Many women, however, did not receive their yearly test because of their inability to visit a doctor on an annual basis, their reluctance to see a doctor or the expense of visiting a doctor coupled with test costs. U.S. Pat. No. 6,302,853 involves one self-administrated cervical sampling system to help solve the problem.

BRIEF SUMMARY

In view of the foregoing, the present disclosure is generally directed to a system for collecting samples of cervical tissue and/or vaginal secretions emanating from a human body.

Aspects of the disclosure include a cervical sampling apparatus for being slidably and rotatably disposed in a vaginal insertion tube include an elongated tubular body having an interior pathway within the tubular body configured to receive an insertable shaft therein. The elongated tubular body having a plurality of opposing resilient locking tabs configured to extend into the interior pathway and engagely lock the insertable shaft within the interior pathway to prevent longitudinal movement of the shaft relative to the interior pathway.

Aspects of the disclosure include a cervical sampler for being slidably and rotatably disposed in a vaginal insertion tube. The cervical sampler includes an elongated body including a pathway configured to receive insertable shaft therein. Further, the elongated body has at least one resilient locking tab configured to extend into the pathway and engagely lock the insertable shaft therein.

Aspects of the disclosure includes a cervical sampling apparatus includes a cervical sampler for being slidably and rotatably disposed in a vaginal insertion tube. A sample collecting member includes a shaft having a removable cervical brush head for obtaining a cervical sample when positioned within the vaginal cavity of a human body; wherein the cervical sampler includes an elongated body including a tubular pathway having at least one resilient locking tab configured to engagely lock the shaft therein.

BRIEF DESCRIPTION OF THE DRAWINGS

The foregoing summary as well as the following detailed description of the invention, considered in conjunction with the accompanying drawings, provides a better understanding of the disclosure, in which like reference numbers refer to like elements, and wherein.

DETAILED DESCRIPTION

Figure 1:
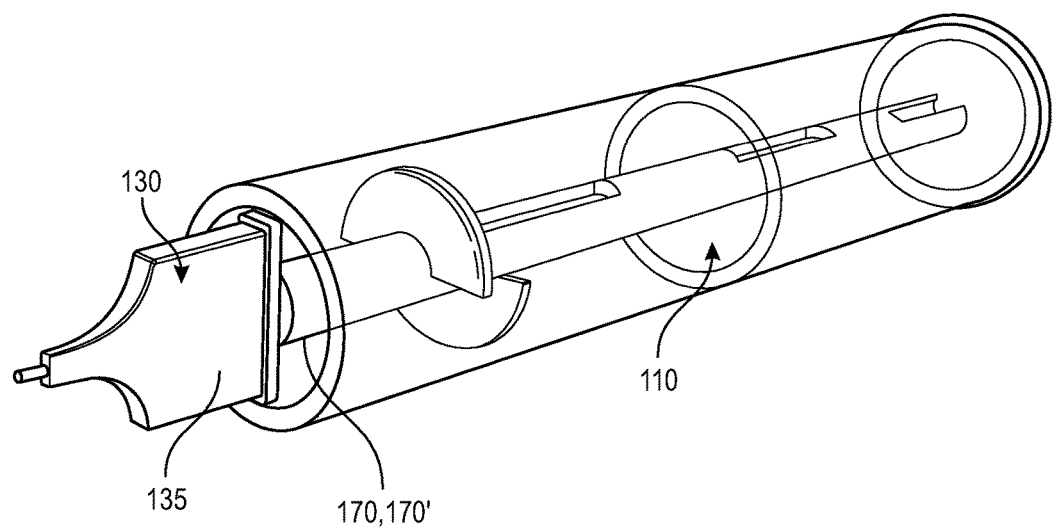
FIG. 1 is a perspective view of an assembled configuration of a cervical sampler and tubular speculum in accordance to the aspects of the disclosure.

FIGS. 1-13 illustrate a portable cervical tissue sample collecting system 100 for at least one use of self-administered sampling of cervical tissue and vaginal fluids of a human. The sample collecting system 100 may include one of more of the following components—a vaginal insertion tube 110, an introduction guide member 120, a sample collecting member 130 attached to a human-operated cervical sampler 170, 170'.

Cervical Sampler

The cervical sampler 170, 170' includes the configured sample collecting member 130 that comes into contact with tissue of the cervix. The sample collecting member 130 removes cervical tissue cells that will be analyzed after the sample collection process has been completed.

Figure 9:
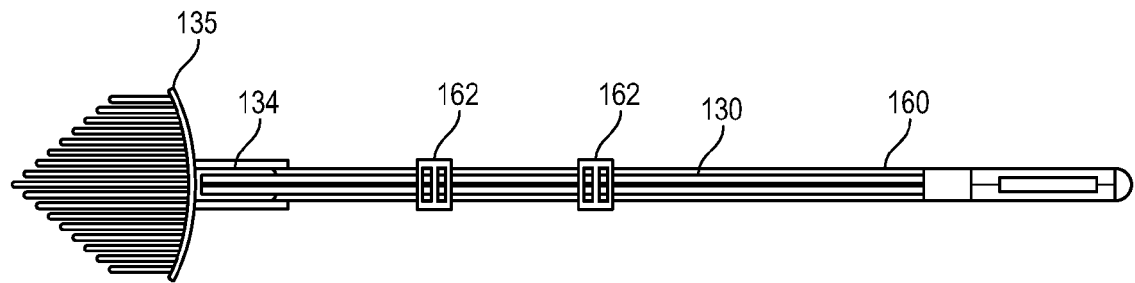
FIG. 9 is a side view of an sample collecting member.
Figure 10:
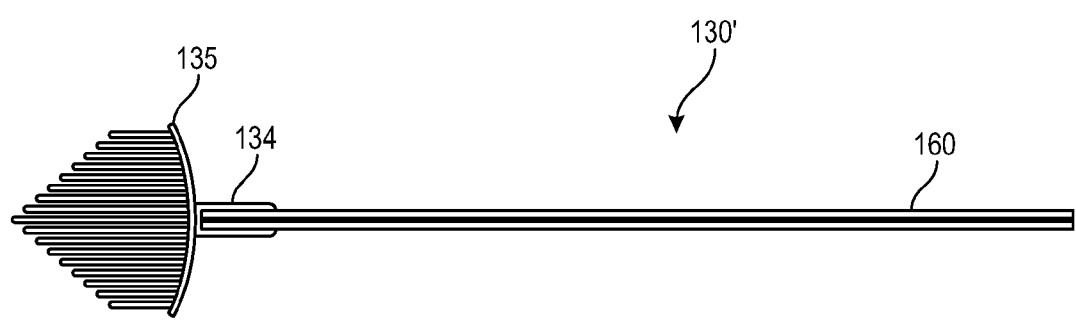
FIG. 10 is a side view of an alternative construction of a sample collecting member.

Referring to FIGS. 1 and 4-7, the sample collecting member 130, in one construction, at a sampling end 132, includes a removable cervical brush head 135 used in gynecological procedures that samples a transformation zone of a cervix, such as the endocervix and ectocervix. The brush may be flexible and designed with many extensions or bristles to collect cervical cells. Brushes which can be used are similar to those manufactured by Wallach Surgical Devices. The sample collecting member 130, however, may include any type of brush, probe, swab or the like which can similarly be used in gynecological cytology to collect a cervical cell specimen. As seen in FIGS. 9 and 10, the sample collecting member 130, 130' includes an elongated shaft 160 extending from the brush head 135. Additionally, the brush head 135 includes a brush collar 134 removably connected to the shaft 160.

Figure 7:
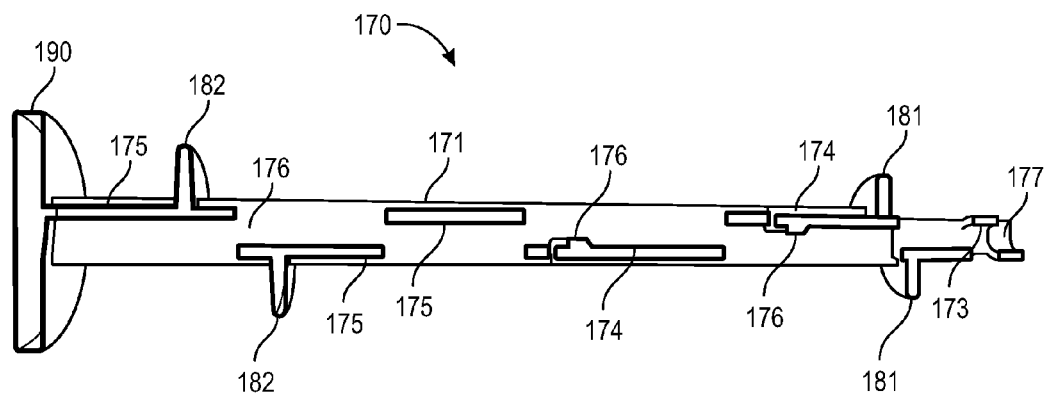
FIG. 7 is a longitudinal sectional view of the embodiment of a cervical sampler shown in FIGS. 4-6.

As best seen in FIG. 7, in one construction, the cervical sampler 170, 170' comprises an elongated tubular body 171 having a hollow interior pathway 172. In a transverse cross section, the tubular body 171 forms a circle shape for the pathway 172, although other cross-sectional shapes are possible. The tubular body 171 includes a plurality of resiliently biased locking tabs 174 being longitudinally disposed along the body 171 and opposed to each other such as 180 degrees. Each locking tab 174 includes a protrusion 176 extending inwardly into the interior pathway 172. The protrusions 176 have a wedge-sloped configuration or a ramp-shape with the lower end facing towards the sample collecting end 132. As seen in FIG. 9, the shaft 160 of the sample collecting member 130 includes two spaced locking ribs 162. Now referring back to FIG. 7, in use, the patient or other person inserts that shaft 160 into the receiving end 132 of the sample collecting member 170. As the shaft 160 is advanced into the pathway 172, the ribs 162 slide upward on the incline and over the far end of the protrusion 176 of the locking tabs 174. Referring to the schematic diagram of FIG. 13, upon further advancement of the shaft 160, the ribs 162 are disposed behind the protrusion 176. In operation of the locking tabs 174, the protrusion 176 of the locking tabs 174 securely engages the locking ribs 162 of shaft 160 of the sample collecting member 130 to provide snap-fit or pressure-fit engagement to prevent forward or backward longitudinal movement of the shaft out of the pathway 174 of the cervical sampler 170. In this way, the cervical sampler 170 can be utilized as a single-use medical device.

The sampling end 132 of the cervical sample 170, 170' includes brush head collar pressure lock 173 configured to engage the brush collar 134 (See FIGS. 9 and 10 for brush collar and FIGS. 4-8 and FIG. 12 for pressure lock 173 feature). The collar pressure lock 173 in the form of two opposing nubs or teeth is configured to grasp onto the brush collar 134 of the brush head 135 (see FIG. 13). This configuration provides for enhanced torsional strength of the assembly of the cervical sampler 170 and the sample collecting member 130.

The sample collection member 130 is utilized for an automated or computer assisted Pap test cytological analysis. The sample collecting member 130 cervical brush head 135 should be smaller in width than the inner diameter of the vaginal insertion tube 110 to allow the cervical brush to fit inside the tube 110.

Figure 8:
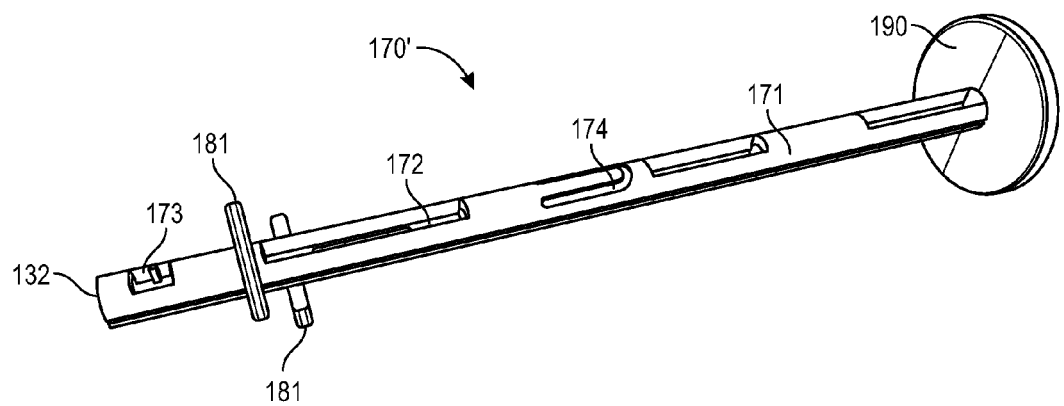
FIG. 8 is a perspective view of an alternative embodiment of a cervical sampler in accordance with the aspects of the disclosure.

Referring to FIGS. 4-7, the cervical sampler 170 includes a front end having semi-circular guide members 181, 182 and a rearwardly disposed disk handle 190. The forward 181 and rear 182 semi-circular guide members are used to guide and to align the cervical sampler 170 along the center longitudinal axis 3 of the vaginal insertion tube 110. The semi-circular guide members 181, 182 move longitudinally and rotationally relative to the insertion tube 110, rather than being fixed to the tube 110. As seen in FIG. 8, an alternative construction of the cervical sampler 170' includes only forward guide members 181 and eliminates rear guide members 182.

Figure 11:
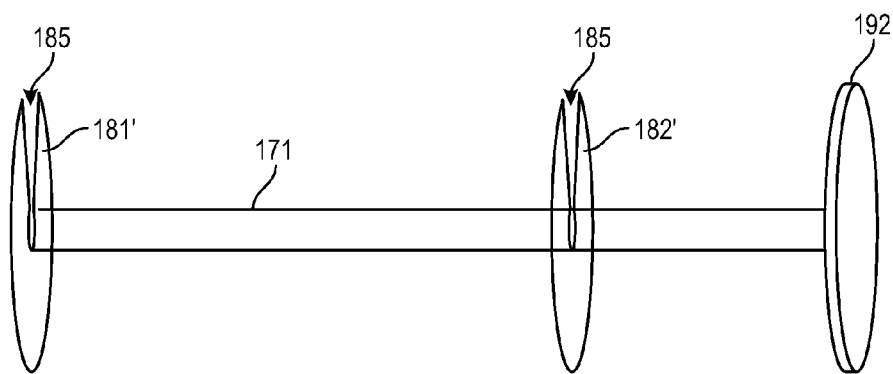
FIG. 11 is a side schematic view of an alternative embodiment of a cervical sampler in accordance with the aspects of the disclosure.
Figure 12:
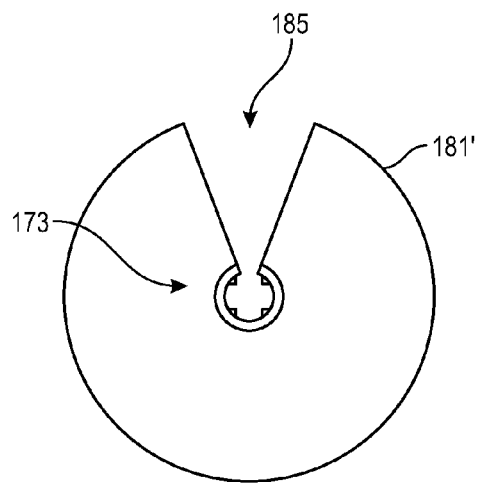
FIG. 12 is a front schematic view of the alternative embodiment of a sample collecting member shown in FIG. 11.
Figure 13:
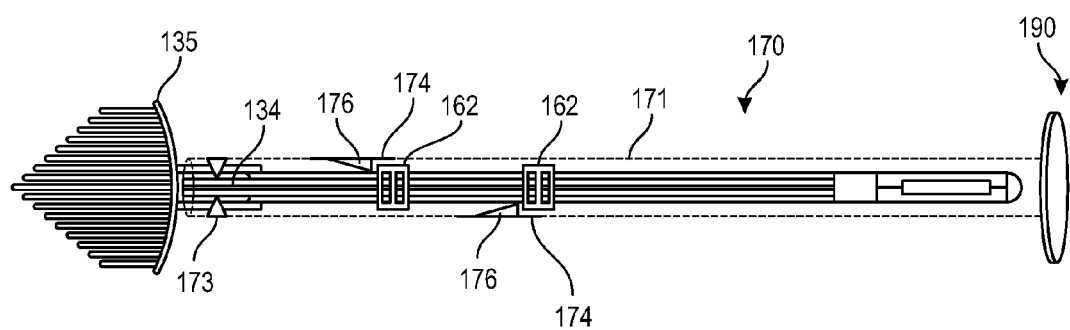
FIG. 13 is a schematic side view of the sample collecting member of FIG. 9 illustrating an interaction with cervical sampler locking mechanisms with the cervical sampler body shown in broken lines.

Referring to FIGS. 4-7, the guide members 181, 182 can be integrally molded and formed with the elongated body 170 as a single unit. The guide members 181, 182 are also positioned perpendicular to the longitudinal axis 177, such that the guide members 181, 182 travel in conjunction with the elongated body whenever the body slides or rotates within the vaginal insertion tube 110. In one construction, the guide members 181, 182 are formed in the shape of a semi-circular disk and may have the same or different diameters. Guide members 181, 182 are disposed in opposing offset directions on the elongated body 171. The semi-circular shape and opposing offset directions helps enable easier insertion of the cervical sampler 170 in to the insertion tube 110 by reducing pressure in the vaginal cavity as a result of providing an open, air fluid escape passageway and reducing pressure on the transformation zone of the patient's cervix. Referring to FIGS. 11-12, the guide member 181', 182' may be of circular shape with wedge shaped cutout 185 or other void shapes therein to provide an air fluid escape passageway.

In a one construction of the sampler 170, the elongated body 171 includes one of more molded stiffening ribs 175 disposed longitudinally (See FIG. 7). These stiffening ribs 175 increase the sectional centroid of the elongated body 171 thereby providing enhanced resistance to buckling under longitudinal applied force during a sampling procedure.

At the rear end of the cervical sampler 170, a center of the disc shaped handle 190 is integrally molded connected to elongated body 171. In one construction, the handle 190 extends radially and perpendicularly from the longitudinal axis 177, and may include a tactile portion, such as a straight knurling pattern (not shown). The handle 190 performs several functions. First, the handle 190 is of sufficient size to allow the patient to grasp the handle 190 and freely rotate the cervical sampler 170 within the vaginal insertion tube 110 and rotate the sample collecting member 130 extending outside the tube 110, in order to collect the necessary cervical cell sample. Second, the handle 190 can be grasped by the patient in order to insert and remove the cervical sampler 150 from the vaginal insertion tube 110. In this manner, the handle 190 controls how far the sample collecting member 130 will extend from vaginal insertion tube 110. In a one construction, the handle 190 has a diameter larger than that of the vaginal insertion tube 110.

The handle 190 includes a rotation indicator 192 in the form of a forward extending protuberance or nub that creates an audible or tactile indication of the completion of a revolution when used in combination with the vaginal insertion tube 110. The rotation indicator 192 extends from the forward face of the handle 190 in the direction of the sample collecting member 130. The rotation indicator 192 substantially contacts a groove 119 of tube 110 (see FIGS. 1 and 4-5), such that the audible or tactile indication is produced and communicated to the user. This indication or signal occurs when the user rotates the rotation indicator 192 past a reference point (e.g. groove 119) during the sampling procedure.

As seen in FIG. 7, cervical sampler 170 can be of an integral molded construction of plastic material using injection molding. The plastic material for the cervical sampler 170 can be lightweight, biocompatible, inert, capable of being sterilized and have a generally smooth surface. The cervical sampler 170 may be constructed from plastic material, such as a high impact polystyrene (HIPS) crystal. It should be noted that cervical sample 170 could also be constructed using 3-D printing technology. The cervical sampler 170 would be defined in a digital 3D computer model. Then a designated 3-D printer processes the digital model to build-up plastic layers of the object (sampler 170) to construct the final product. This build-up process is known in the technology art as additive manufacturing.

In the cervical sampler 170' shown in FIGS. 11-12, it can be of a molded plastic material like sampler 170 or 3-D printers. In lieu of plastic, cervical sampler 170' can be constructed of a biocompatible paper material used in medical field. The paper construction of the tubular body 171 of sampler 170' would have a wall thickness sufficient to prevent buckling when sample collecting member 130' is advanced into the body 171. Further, the guide members 181', 182' can be of a sufficient thickness and can be attached to the tubular body 171 when a biocompatible adhesive.

Vaginal Insertion Tube

Figure 3:
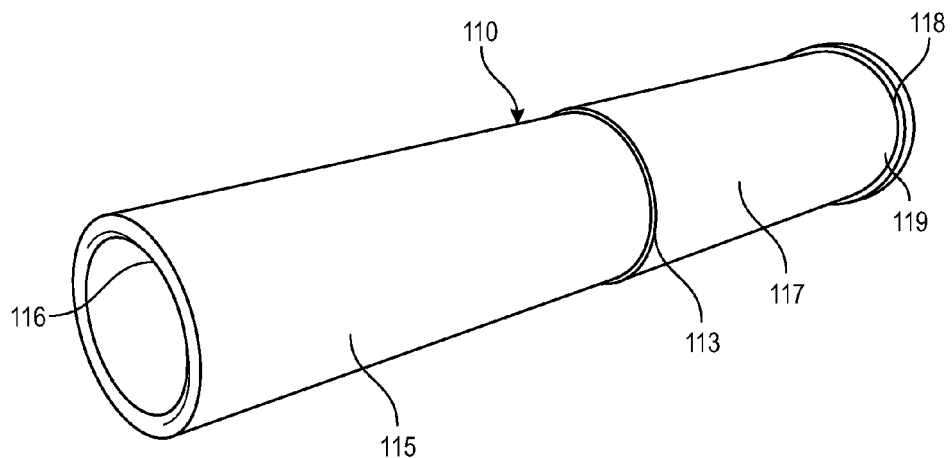
FIG. 3 is a perspective view of the tubular speculum constructed in accordance with the aspects of the disclosure.
Figure 4:
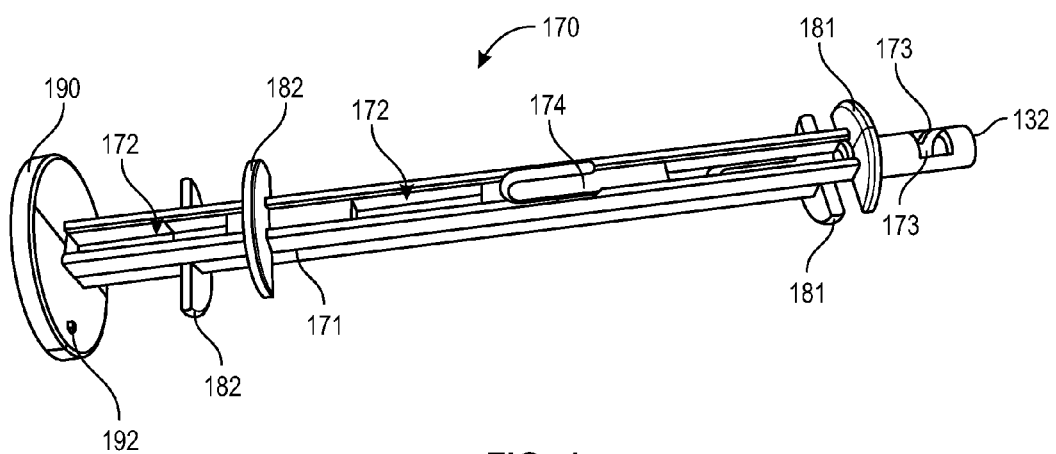
FIGS. 4-6 are views of one embodiment of a cervical sampler in accordance with the aspects of the disclosure.
Figure 5:
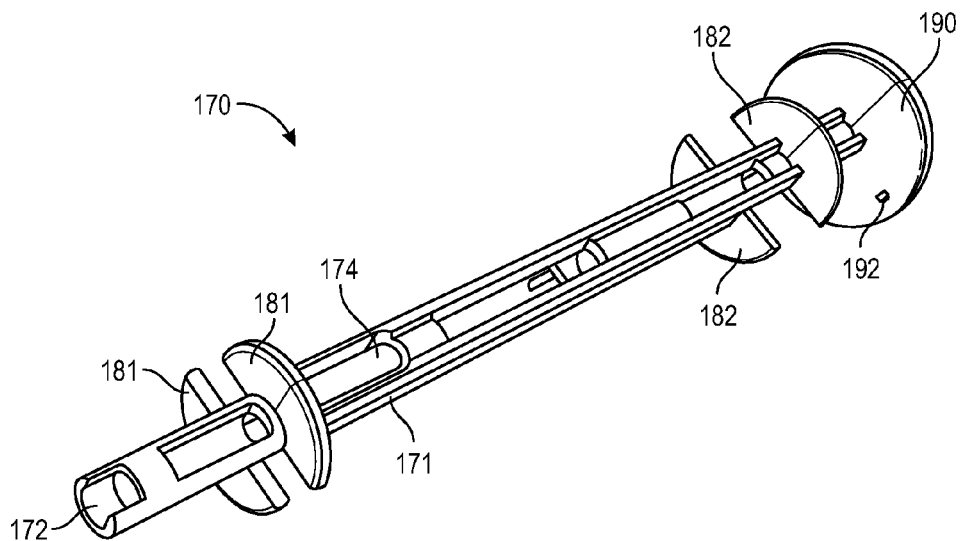
Figure 6:
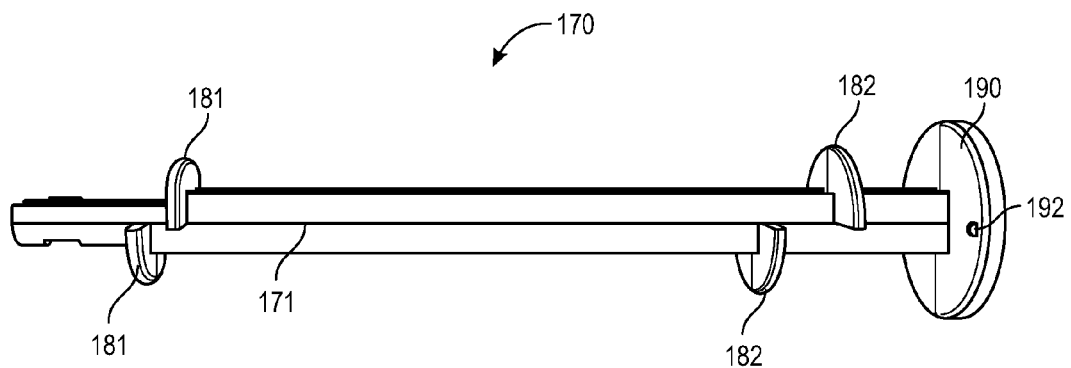

Referring to FIG. 3, the vaginal insertion tube 110 servers as a tubular speculum configured for opening the vaginal cavity of a patient and providing a passageway in order to collect a cervical tissue sample. The vaginal insertion tube 110 includes an insertion position indicator 113 and center axis 114. In a one construction, the vaginal insertion tube 110 also includes a forward cylinder section 115 and a rear cylinder section 117. In cross-section taken perpendicular to a longitudinal axis, the forward cylinder section 115 and a rear cylinder section 117 of the tube 110 is circular. The forward cylinder section 115 includes a proximally disposed edge 116 of a general round construction.

The tube 110 also includes an insertion position indicator 113 having a tactile portion around its outer circumference. The insertion position indicator 113 allows the patient to easily and reliably determine the appropriate depth to insert the vaginal insertion tube 110. The insertion position indicator 110 may include any surface discontinuity such as a surface depression, a step between the forward cylinder section 115 and the rear cylinder section 117, as shown in the figures, or a variance in surface texture on the surface of the tube 110. This feature enables the patient to better judge the depth of insertion into the vaginal cavity by alerting her when about half of the tube 110 has been inserted. Further the insertion position indicator 110 allows the patient to feel the location of the tube relative to the outer tissue of the vagina.

The distal rear end of the rear cylinder section 117 of the vaginal insertion tube 110 has a flange 118 with a groove or notch portion 119. The groove 119 operates in conjunction with rotation indicator 192 of the handle 190 of the cervical sampler 170 as discussed below. The physical interaction of the rotation indicator 192 and groove 119 provide an audible and tactile indication each time the user rotates the cervical sampler 170 through a complete revolution and past a reference point.

Dimensionally, from the larger diameter distal end to the small diameter proximal end, vaginal insertion tube 110 has one degree taper. In one construction, the diameter of the distal end can be 1.050 inches and the diameter of the proximal end can be 1.025 inches.

Introduction Guide Member

Figure 2:
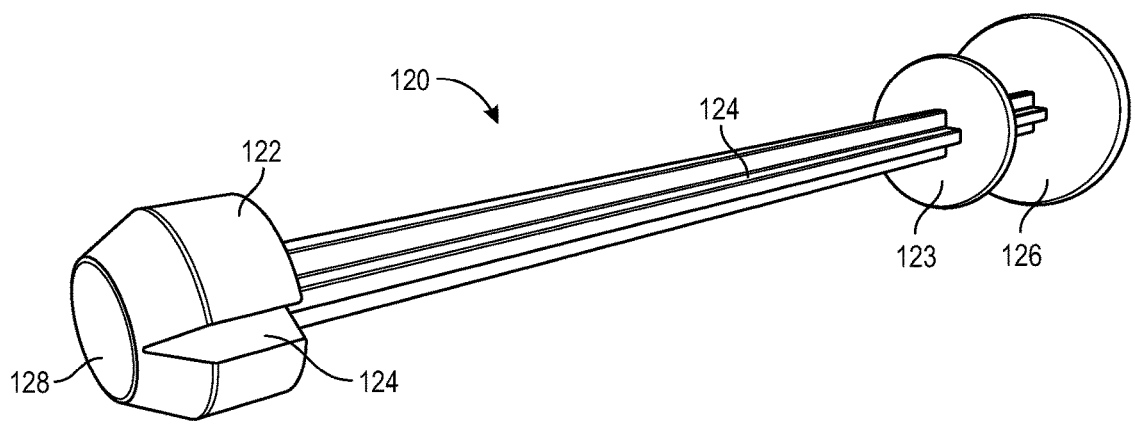
FIG. 2 is a perspective of an introduction guide member accordance with the aspects of the disclosure.

Referring to FIG. 2, the introduction guide member 120 when inserted in the vaginal insertion tube 111 assists in distending the vaginal cavity. The introduction guide member 120 includes a proximally disposed guide head 122 attached to an elongated shaft 124 and a handle 126 at a distal rear end. The guide head 122 includes a tapered-edge nose cone portion 128 integrally formed with a cylinder portion 129. A leading edge of the nose cone portion 128 is flat so that the user will not be injured by a sharp or pointed edge during insertion. In one construction, the nose cone portion 128 may include a taper which is generally aligned a tapered proximal edge of tube 110 to create a smooth transition between these elements and provide for comfortable and easy insertion of the introduction guide member 120 into the vaginal cavity. Introduction guide member 120 may be constructed of a molded plastic material.

The guide head 122 includes at least one air passageway 124 therein to enable for easier insertion of the vaginal insertion tube 110. This construction is useful when the introduction guide member 120 in place within the vaginal insertion tube 110. The air passageway 124 reduces air pressure in the vaginal cavity as a result of providing an open, fluid escape passageway from the forward face of the guide head 122.

The introduction guide member 120 includes at least one disk shaped tube guide 123 integrally formed with the elongated shaft 124. The tube guide 123 assists in providing lateral stability to the introduction guide member 120 and assists in aligning the guide member 20, when the guide member 120 is inserted into the vaginal insertion tube 110.

The plastic material for the vaginal insertion tube 110 and introduction guide member 120 should be lightweight, biocompatible, inert, capable of being sterilized and have a generally smooth surface. The vaginal insertion tube 110 is constructed from plastic material, such as a high impact polystyrene (HIPS) crystal. The vaginal insertion tube 110 and the introduction guide member 120 are manufactured or formed in a process such as, injection molding. Injection molding is one manufacturing process used to form the above mentioned components. Alternatively, the tube 110 and introduction guide member 120 may be constructed using 3-D printing technology in lieu of injection molding. In such a case, the tube 110 and member 120 may be of a printed plastic material construction.

Operational Method

Referring to FIGS. 1-5, an overview of a manner of operating the sample collecting system 100 in accordance with the aspects of the disclosure follows. A pre-insertion assembly is formed by placing the introduction guide member 120 within the vaginal insertion tube 110. The assembly is then inserted into a patient after they assumes a predetermined desired position. Once the insertion tube 110 has been inserted to an appropriate depth, such as the midpoint of the total insertion distance, the introduction guide member 120 is removed from the vaginal insertion tube 110.

The advancing of tube 110 is continued until it is positioned within the vaginal cavity at a sampling position where the front end of the vaginal insertion tube 110 is located immediately in front of the cervix. The cervical sampler 150 is then inserted into the vaginal insertion tube 110. The sample collecting member 130 is pushed into contact with cervical tissue, and a cervical tissue sample is collected by rotating the cervical sampler 170. The cervical sampler 170 is then removed from the vaginal cavity and the cervical tissue sample is transferred from the sample collecting member 130 to a collection container that retains a preservative solution. The collection container is packaged and sent to a predetermined laboratory for analysis. After the sample has been analyzed, the results can be communicated back to the patient.

The patient or user fully inserts the introduction guide member 120 into the vaginal insertion tube 110 to form the pre-insertion assembly. The patient also performs a maneuver, on a substantially horizontal surface, by lying down on her back with her knees bent upward (a modified situp position) in which the pelvic floor of the patient is depressed. This maneuver advantageously allows the cervix to align with the tube 110 due to the added effect of creating abdominal pressure during the insertion of the introduction guide member 120 and vaginal insertion tube 110, coupled with the depression of the pelvic floor.

Next, the patient slowly inserts the introduction guide member 120 and vaginal insertion tube 110 into their vagina in order to distend the vaginal cavity and generally aligns the axis of the tube 110 with the cervix of the patient. The introduction guide member 120 and vaginal insertion tube 110 are advanced together until the insertion depth indicator 113 is proximate the vaginal walls. When the midpoint depth is reached, the introduction guide member 120 is withdrawn from the vaginal insertion tube 110. During the removal of the guide member 120, the patient retains the position of the tube 110 in the vaginal cavity. After the introduction guide member 120 is removed, the patient further advances the tube 110 into the vaginal cavity until the tube 110 is in a sampling position at the cervix and resistance is felt by the patient. The position of the vaginal insertion tube 110 is maintained and the patient inserts the cervical sampler 170 into the tube 110.

The patient then applies pressure to the cervical sampler 170 thereby contacting a portion of the cervix with the sample collecting member 130. Next, the patient maintains the position of the vaginal insertion tube 110 and rotates the handle 190 between 5 and 15 complete revolutions. Depending on brush designs more or less rotations could be employed. In a one construction, the handle 190 is rotated through ten (10) complete revolutions. In turn, the sample collecting member 130 will also be rotated ten revolutions so as to collect cervical samples. This feature is advantageous to determining the amount of cervical sample collected.

In one construction, after the appropriate number of rotations, such as ten, an appropriate amount of cervical sample has been collected. The patient removes the cervical sampler 170 from the vaginal insertion tube 110, and subsequently withdraws the vaginal insertion tube 110 from the vaginal cavity. In a one construction, the sample collection member 130 is then pulled away from the shaft 160 and brush collar 173 and thus is removed from the remainder of the cervical sampler 170 and placed into a collection container, such as a vial, that retains an ethanol based liquid thin layered preservative solution used in gynecological cytology, such as AutoCyte PREP. This method advantageously allows for using substantially automated screening of the cervical sample to reduce the diagnosis problems associated with a manual method of screening. In general, the above preservative solutions provide for preservation of cervical cells for future analysis in gynecological cytology. Once the sample is collected, the collection container is sealed, labeled and transported to a predetermined laboratory for analysis. In a one construction, the laboratory includes automated or computer assisted diagnosis equipment for analysis of the cervical sample collected by the patient. After the cells have been transferred to the solution or analyzed, the sample collecting member 130 may discarded. Once the laboratory completes the analysis of the cervical sample, the results are communicated back to the patient.

System 100 has a configuration in which the components can be configured operate together. All U.S. patents referred to in this application are fully incorporated by reference for all purposes. While the apparatus and methods has been described with reference to exemplary embodiments, it will be understood by those of ordinary skill in the art that various changes may be made and equivalents may be substituted for elements thereof without departing from the scope of the disclosure. In addition, many modifications may be made to adapt a particular situation or material to the teachings of the invention without departing from the scope thereof. Therefore, it is intended that the invention not be limited to the particular embodiments disclosed, but that the invention will include all embodiments falling within the scope of the appended claims.

What is claimed is:

1. A cervical sampling apparatus, comprising:
    a cervical sampler configured for being slidably and rotatably disposed in a vaginal insertion tube,
    wherein the cervical sampler includes:
        an elongated body including an interior pathway configured to receive an insertable shaft therein, the elongated body having opposing resilient locking tabs disposed longitudinally and configured to extend into the interior pathway to engagely lock the insertable shaft therein;
        a plurality of offset guide members pairs disposed longitudinally on the elongated body and over the interior pathway so that the pathway is open for receiving the insertable shaft therein, the guide members being disposed transverse to a longitudinal axis of the elongated body so to slidably engage the vaginal insertion tube; and
        a sample collecting member disposed at a distal end of the insertable shaft configured for obtaining a cervical sample when positioned within the vaginal cavity of a human body.

2. The apparatus of claim 1, wherein the sample collecting member comprises a cervical brush head being releasable for the insertable shaft for obtaining a cervical sample when positioned within the vaginal cavity of a human body.

3. The apparatus of claim 2, wherein a distal end of the elongated body of the cervical sampler includes a collar lock extending into the interior pathway so as to engage the sample collecting member.

4. The apparatus of claim 1, wherein the elongated body of the cervical sampler includes at least one stiffening rib extending in a longitudinal direction.

5. The apparatus of claim 1, wherein the guide members have a semi-circular shape.

6. The apparatus of claim 1, wherein the elongated body of the cervical sampler includes a circular handle.

7. The apparatus of claim 1, wherein the guide members provides an air pressure escape passageway during use with the vaginal insertion tube.

8. The apparatus of claim 1, wherein the insertable shaft includes a plurality of ribs configured to engage the resilient locking tabs of the elongated body.

9. The apparatus of claim 1, wherein at least one of the resilient locking tabs of the elongated body includes a protrusion having a ramp portion facing towards a sample collecting end of the elongated body.

10. A cervical sampling apparatus, comprising:
an elongated tubular body including an longitudinal axis and an interior pathway within the tubular body configured to receive an insertable shaft therein, the elongated tubular body having a plurality of opposing resilient locking tabs configured to extend into the interior pathway and engagely lock the insertable shaft within the interior pathway to prevent longitudinal movement of the shaft relative to the interior pathway; and
at least one pair of offset guide members disposed longitudinally on the elongated body and over the interior pathway so that the pathway is open for receiving the insertable shaft therein, the guide members being disposed transverse to the longitudinal axis of the elongated tubular body; the guide members being slidably and rotatably engagable within a vaginal insertion tube.

11. The apparatus of claim 10, further comprising the insertable shaft having a sample collecting member disposed at a distal end for obtaining a cervical sample when positioned within the vaginal cavity of a human body.

12. The apparatus of claim 11, wherein the elongated body includes a collar lock configured to engage an exterior portion of the sample collecting member.

13. The apparatus of claim 10, wherein the elongated body of the cervical sampler includes at least one stiffening rib extending in a longitudinal direction.

14. The apparatus of claim 10, guide member extending from the elongated body has a semi-circular shape.

15. The apparatus of claim 10, wherein the elongated body of the cervical sampler includes a circular handle.

16. The apparatus of claim 10, wherein the guide members provides an air pressure escape passageway during use with the vaginal insertion tube.

17. The apparatus of claim 10, wherein the insertable shaft includes a plurality of ribs configured to engage the resilient locking tabs of the elongated body.

18. The apparatus of claim 10, wherein at least one of the resilient locking tabs of the elongated body includes a protrusion having a ramp portion facing towards a sample collecting end of the elongated body.

19. The apparatus of claim 10, further comprising at least two pairs of offset guide members disposed longitudinally on the elongated body and over the interior pathway.

* * * * *